United States Patent
Yoshida et al.

[11] Patent Number: 5,805,160
[45] Date of Patent: Sep. 8, 1998

[54] DIAGNOSTIC APPARATUS HAVING A SYMPTOM EVALUATION PROCESSING FUNCTION TO IMPROVE CAUSE HYPOTHESIS

[75] Inventors: Hiroyuki Yoshida; Yuko Nakayama; Rieko Yamamoto, all of Kawasaki, Japan

[73] Assignee: Fujitsu Limited, Kawasaki, Japan

[21] Appl. No.: 751,957

[22] Filed: Nov. 19, 1996

Related U.S. Application Data

[63] Continuation of Ser. No. 301,401, Sep. 8, 1994, abandoned.

[30] Foreign Application Priority Data

Dec. 6, 1993 [JP] Japan .................................. 5-305290

[51] Int. Cl.[6] ........................................................ G06F 3/00
[52] U.S. Cl. ........................ 345/339; 395/10; 395/183.01
[58] Field of Search ..................................... 345/339, 965, 345/966, 970; 395/1, 10, 11, 12, 183.01, 183.02, 183.22, 911, 922

[56] References Cited

U.S. PATENT DOCUMENTS

| | | |
|---|---|---|
| 4,697,243 | 9/1987 | Moore et al. . |
| 5,070,468 | 12/1991 | Niinomi et al. . |
| 5,138,694 | 8/1992 | Hamilton ................................. 395/10 |
| 5,187,773 | 2/1993 | Hamilton et al. . |

OTHER PUBLICATIONS

Peng, Y. et al, "A Connectionist Model for Diagnostic Problem Solving," IEEE Trans. SMC, V. 19, No. 2, 1989, pp. 285–298.

Peng, Y. et al, "A Probabilistic Causal Model for Diagnostic Problem Solving–..." IEEE Trans. SMC, V. 17, N. 2, 1987, pp. 146–162.

Kane et al, "AI in Medicine," AI Expert, Nov. 1988, pp. 48–55.

*Primary Examiner*—A. Katbab
*Attorney, Agent, or Firm*—Staas & Halsey

[57] ABSTRACT

A diagnosis apparatus includes a user interface (UI) control processing unit provided as a user's interface, a plurality of symptom evaluation processing unit operatively connected in parallel to the UI control processing unit, and a display unit operatively connected to the UI control processing unit. The UI control processing unit sequentially broadcasts symptoms to all symptom evaluation processing unit. Each symptom evaluation processing unit carrys a different symptom specified in advance for every processing unit, and evaluates a hypothesis for a cause of the symptom in order to execute an optimum search operation for the symptom.

8 Claims, 7 Drawing Sheets

DIAGNOSTIC APPARATUS HAVING A SYMPTOM EVALUATION PROCESSING FUNCTION TO IMPROVE CAUSE HYPOTHESIS

This application is a continuation of application Ser. No. 08/301,401, filed Sep. 8, 1994, now abandoned.

BACKGROUND OF THE INVENTION

1. Field of the Invention

The present invention relates to a diagnosis apparatus, and particularly, it relates to a diagnosis apparatus which can resolve very difficult and complicated diagnosis problems, for example, problem of medical diagnosis, failure diagnosis of nuclear reactors, and the like, which require high-level knowledge and experience of an expert.

2. Description of the Related Art

Recently, knowledge engineering is known as a technique for using knowledge accumulated by experts for use in computers. In general, an expert's knowledge is gathered through interviews with the expert, and the knowledge is assembled in a particular form for use in a computer (i.e., is computerized). However, it is hard to computerize such knowledge based on the experience of experts.

Accordingly, the present invention aims to easily computerize knowledge gained by experts by utilizing knowledge engineering. Particularly, the diagnosis apparatus according to the present invention can easily resolve complicated medical diagnosis problems which require high-level knowledge and experience of an expert.

SUMMARY OF THE INVENTION

The object of the present invention is to provide a diagnosis apparatus which can easily resolve very difficult and complicated diagnosis problems which require high-level knowledge and experience of an expert by utilizing knowledge engineering.

In accordance with the present invention, there is provided a diagnosis apparatus including a user interface (UI) control processing unit, plurality of symptom evaluation processing units operatively connected in parallel to the UI control processing unit, and a display unit operatively connected to the UI control processing unit. The UI control processing unit sequentially broadcasts symptoms given by the user to all symptom evaluation processing units, while each symptom evaluation processing unit carries a different symptom specified in advance for every processing unit, calculates a hypothesis of possible causes (cause hypothesis), and evaluates the symptom in order to execute an optimum search operation of symptoms.

In a preferred embodiment, the UI control processing unit comprises a symptom evaluation display unit for receiving results of evaluation from the symptom evaluation processing units, and outputting them to the display unit in order to support selection of the symptom by the user; a cause hypothesis display unit for receiving the cause hypothesis sent from the particular symptom evaluation process unit, and outputting it to the display unit in order to inform the cause hypothesis to the user; and a symptom input unit for broadcasting the symptom selected by the user to all symptom evaluation processing units.

In another preferred embodiment, each of said symptom evaluation processing units comprises: a hypothesis preparation unit for obtaining the cause hypotheses $D(F)$ and $D(F \cup \{f\})$ for a set "F" of symptoms and a symptom "f"; and a symptom evaluation unit for obtaining an evaluation $E(f:F)$ of the symptom "f" for the set $F$ of symptoms by using the cause hypotheses.

In still another preferred embodiment, the UI control processing unit further comprises a re-arrangement unit for re-arranging the symptom evaluation processing units into a predetermined number of groups corresponding to the number of processors.

In still another preferred embodiment, the symptom evaluation display unit displays evaluation values sent from the symptom evaluation processing units in the order of importance on a screen of the display apparatus.

In still another preferred embodiment, the symptom evaluation display unit divides the evaluation values into a predetermined number of groups in the order of importance, and displays them on the screen.

In still another preferred embodiment, when the symptom carried out by the symptom evaluation unit is previously and fixedly determined for each unit, the symptom evaluation can be optimized in accordance with the symptom carried out thereby.

In still another preferred embodiment, the symptom carried out by the symptom evaluation unit is dynamically re-arranged so that it is possible to perform load distribution of the system.

DESCRIPTION OF THE PREFERRED EMBODIMENTS

Figure 1:
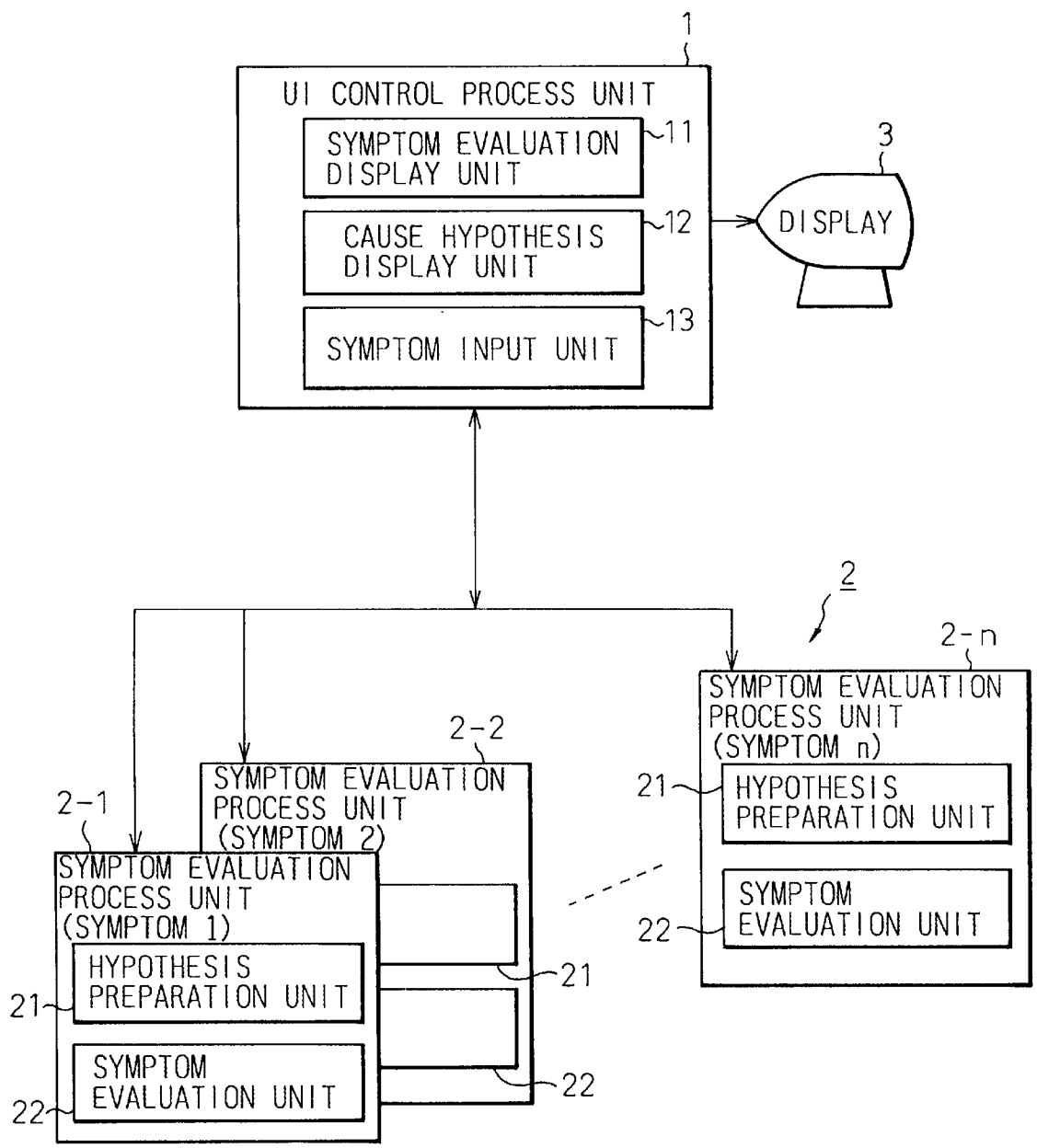
FIG. 1 is a schematic block diagram of a diagnosis apparatus according to an embodiment of the present invention.

Before describing the preferred embodiments, a conventional art and its problem will be explained in detail below.

In general, there are two kinds of knowledge necessary for making a medical diagnosis. The first kind is the knowledge necessary to develop a hypothesis of a possible cause based on a set of various symptoms which are obtained by a doctor. The second kind is the knowledge used in a method for pursuing the symptoms.

The following explanation is given for the first knowledge for making a medical diagnosis. As examples of the symptoms, two symptoms are considered, i.e., "a slight fever" (symptom: f1), and "a positive reaction to a BCG test" (symptom: f2). As possible causes for these symptoms, two causes are considered, i.e., "a cold" (cause: d1), and "tuberculosis" (cause: d2).

A typical example of developing a hypothesis to pursue possible causes (below, this is called "cause hypothesis") is expressed by numbers which indicate possibility (i.e., level of possibility) of each cause as follows. For example, numbers indicating possibility are attached to the causes d1 to d3 as follows.

$$\{d1:60\%, d2:1\%, d3:10\%, \ldots\}$$

In this case, the unit of each number is "%".

A doctor examines a patient, and obtains a set "F" of symptoms which the patient describes as follows.

$$F0=\{f1, f4, f6, f7, \ldots\}$$

The doctor then prepares a cause hypothesis "H" for the set of symptoms F0.

$$H0=\{d1:60\%, d2:1\%, d3:10\%, \ldots\}$$

The relationship between the set F and the factor hypothesis H can be expressed by a function "D" as follows:

$$H=D(F)$$

As is obvious from the above, if it is possible to express the function D in a form which utilizes a computer (i.e., a computerized form), the first knowledge used for medical diagnosis can be computerized.

On the other hand, it is relatively easy for an expert (i.e., a doctor) to offer a cause hypothesis H, for example, regarding a general symptom (for example, "a slight fever"), or a more specific symptom (for example, "a positive reaction to a BCG test").

In the present invention, the expression of the function D by using a computer is based on the typical cause hypotheses which are obtained from an expert. Regarding concrete methods, there is a method of utilizing an expert system which uses a set of rules, for example, "symptom condition (if)" and "result of reasoning to develop the cause hypothesis (then)", and the other is a method of searching for the frequency of occurrence of symptoms which occurred in the past and which are similar to the current symptoms.

The second kind of knowledge necessary for performing a medical diagnosis is utilized in a method of pursuing a symptom. As explained above, the cause hypothesis H for the set F of symptoms is expressed by "H=D (F)". Symptoms which are not included within the set F of the symptoms, but which are considered to be very effective for improvement of the cause hypothesis, are sequentially searched for in this method. As a result, it may be possible to quickly and correctly develop a cause hypothesis. Although almost experts can effectively utilize this method, it is considered to be very difficult to extract this knowledge.

Accordingly, in general, typical search processes are found by using observation and interviews with experts, and symptoms are searched for in accordance with such search processes. However, in the computerized search processes using this method, a user can input the symptoms only in accordance with fixed sequences so that the input operation for an urgent symptom must be input in turn. Further, it is very difficult to cancel or revise symptoms once they are input so that it is necessary to re-input the symptoms from the beginning.

However, if it is possible to define correct change (i.e., change of possibility, %) of the cause hypothesis, it is possible to easily obtain the search method for the symptom. For example, when a patient gives symptoms expressed by the following formula, $$F0=\{f1, f4, f6, f7, \ldots\}$$

The cause hypothesis H0 at that time is defined as follows.

$$H0=D(F0)=\{d1:60\%, d2:1\%, d3:39\%\}$$

Next, it is determined which should be investigated between the symptoms f2 and f3. In this case, it is assumed that the same cost is necessary for determining the symptoms f2 and f3, and this cost cannot be ignored. The doctor must determine as to which may be effective test. If the symptom f2 is confirmed as the effective test, the cause hypothesis H is changed as follows.

$$D(F0 \cup \{f2\})=\{d1:0\%, d2:99\%, d3:1\%\}$$

If the symptom f3 is confirmed, the cause hypothesis H is changed as follows.

$$D(F0 \cup \{f3\})=\{d1:65\%, d2:1\%, d3:34\%\}$$

Further, an evaluation function E(f:F) is defined and is referred to as a contribution rate evaluation function. This function defines which symptom is useful for the diagnosis. Accordingly, this function E can evaluate the symptoms which are not included within the set F of the present symptoms.

The following items are used for evaluation, i.e., the present cause hypothesis H=D(F), the cause hypothesis D (F U {f}) which was changed by the symptom "f", the cost for the investigation of the symptom f, and the possibility (probability) of finding the symptom f.

For example, when the function E is defined by only a sum of absolute values obtained by changing the possibility (%) of each cause "d", the evaluation function can be expressed based on the formulae D(F0), D(F0 U {f2}) and D(F0 U {f3}) (i.e., the large absolute values) mean that the symptoms which change the cause hypothesis as much as possible appear to be acceptable).

$$E(f2:F0)=60+98+38=196$$

In this formula, each numeral is calculated as follows.

$$60=|0-60|, 98=|99-1|, \text{ and } 38=|1-39| E(f3:F0)=5+0+5=10$$

In this formula, each numeral is calculated as follows.

$$5=|65-60|, 0=|1-1|, \text{ and } 5=|34-39|$$

On the other hand, when the evaluation function E is defined only for an increment (decrement is not evaluated) of possibility (%) for the least likely cause "d" within the present cause hypotheses, the evaluation function E can be expressed as follows (i.e., this value means that the symptom, which compensates the cause hypothesis as much as possible, appears to be acceptable), $$E(f2:F0)=98$$

In this formula, the result "98" is calculated by |99−1|

$$E(f3:F0)=5$$

In this formula, the result "5" is calculated by |65−60|

Accordingly, if this evaluation function E can be expressed on the computer, the second type of knowledge necessary for resolving the medical problem can be realized on the computer.

As is obvious, in the process of searching for symptoms, if the evaluation function E(f:F) can be calculated for all symptoms, it is possible to realize an optimum search process. However, the amount of calculations required for the evaluation function is very large, particularly, in the initial stage of the diagnosis. On the other hand, since the evaluation function calculations can be independently carried out for each symptoms, it is considered that these calculations can be executed in parallel. However, there are problems with parallel calculations as explained below.

The first problem lies in an amount of data. Since the amount of data which must be broadcast to the symptom evaluation processing units exerts a large influence on the execution speed of all processes, it is necessary to avoid broadcasting to the symptom evaluation process as to all sets F of the symptoms which are already input.

The second problem lies in a distribution of loads. If the symptom evaluation processing units are not provided in sufficient number for the number of symptoms, any one symptom evaluation processing unit must deal with multiple symptoms. Accordingly, there is a problem of load unbalance among symptom evaluation processing units.

The third problem lies in the processing of evaluation results. For example, when sorting processes are executed after all evaluation results are obtained, the execution speed may be reduced to that of the slowest process.

Accordingly, the object of the present invention lies in resolution of the above three problems. In the diagnosis apparatus according to the present invention, when resolving a diagnosis problem which derives the cause hypothesis H=D (F) from the set F of the given symptoms "f", the definition of the symptoms which would be the most useful for the diagnosis from among the symptoms which are not included in the set F, is executed in parallel.

FIG. 1 is a schematic block diagram of a diagnosis apparatus according to an embodiment of the present invention. The diagnosis apparatus includes a UI (User Interface) control processing unit 1, a plurality of symptom evaluation processing units 2 (2–1 to 2–n), and a display device 3. The UI control processing unit 1 comprises a symptom evaluation display unit 11, a cause hypothesis display unit 12 and a symptom input unit 13. Each symptom evaluation processing unit 2 is separately provided for each symptom, and each comprises a hypothesis preparation unit 21 and a symptom evaluation unit 22.

The symptom evaluation processing unit 2 holds the set F of the symptoms which are sent from the symptom input unit 13. The hypothesis preparation unit 21 prepares the set F of the symptoms, and the cause hypotheses D(F) and D(F U {f}) for the symptom f. The symptom evaluation unit 22 obtains the symptom evaluation E(f:F) for the set F of the symptoms by using these cause hypotheses.

The symptom input unit 13 is used as a user interface, and broadcasts (i.e., transfers) the symptoms selected by the user in parallel to all symptom evaluation processing units 2–1 to 2–n. The cause hypothesis display unit 12 displays the cause hypotheses, which are sent from particular symptom evaluation processing units 2, to the user. Further, the symptom evaluation display unit 11 collects the results of evaluation which are sent from the symptom evaluation processing units 2, and supports selection of a symptom by the user.

The function D of the set F is realized by the hypothesis preparation unit 21 of the symptom evaluation process 2. The hypothesis preparation unit 21 holds a table which includes the symptoms and causes gathered from many examples of symptoms in the past, searches the past examples having the same symptom in the given set F of the symptoms, and determines an occurrence frequency of the cause as the cause hypothesis. For example, when the set F is given as follows, F={f1, f2, f3} the hypothesis preparation unit 21 searches the table, and picks up the past examples of symptoms related to three symptoms f1, f2 and f3. For example, it is assumed that 100 examples of past symptoms exist in total. In these symptoms, when ten causes are represented by d1, fifty causes are represented by d2, and forty causes are represented by d3, the factor hypothesis H for the set F of the symptoms can be expressed as follows H=D(F)={d1:10%, d2:50%, d3:40%}.

The evaluation function E is realized in the symptom evaluation unit 22. The symptom evaluation unit 22 starts the hypothesis preparation unit 21 and obtains the cause hypotheses D(F) and D(F U {f}), and evaluates the symptom f by taking into account the possibility of occurrence and of the symptom f. In this case, the symptom, which gives influence to the possibility of the least likely cause, appears to be useful. That is, the useful symptoms are expressed by a sum of multiplying an absolute values of change (i.e., subtraction) of causes by the possibility of the present cause hypothesis. For example, the cause hypothesis D(F) is defined for the set F of the present symptoms as follows.

D(F)={d1:60%, d2:1%, d3:39%}

When the symptom f2 is confirmed, the cause hypothesis is changed as follows.

D(F U {f2})={d1:0%, d2:99%, d3:1%}

On the other hand, when the symptom f3 is confirmed, the cause hypothesis is changed as follows.

D(F U {f3})={d1:65%, d2:1%, d3:34%}

The evaluation functions E are obtained based on the above formulae D(F), D(F U {f2}), and D(F U {f3}) as follows.

E(f2:F)=(60−0)×0.6+(99−1)×0.01+(39−1)×0.39=51.8

E(f3:F)=(65−60)×0.6+(1−1)×0.01+(39−34)×0.39=4.95

Accordingly, contribution rate becomes high in the symptom f2.

Figure 2:
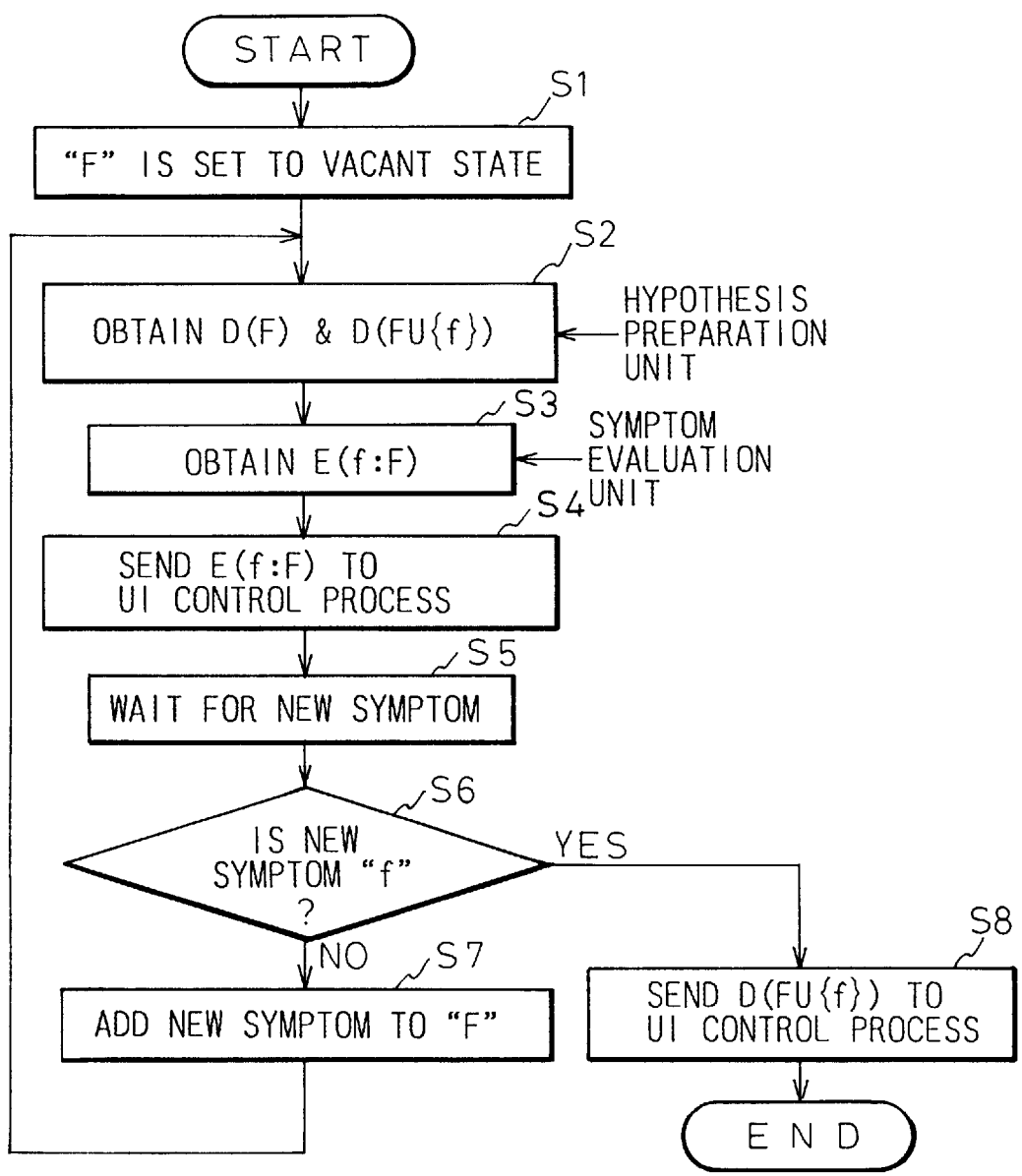
FIG. 2 is an operation flowchart of a symptom evaluation process.

FIG. 2 is an operation flowchart in the symptom evaluation process. This flowchart shows operation steps of the symptom evaluation process which deals with the particular symptom f. Initially, the set F of the symptoms is set to vacant state (step S1), and the hypothesis preparation unit 21 obtains the cause hypotheses D(F) and D(F U {f}) (step S2). Further, the symptom evaluation unit 22 obtains the symptom evaluation E(f:F) (step S3), and sends this symptom evaluation E to the UI control processing unit 1 (step S4). Still further, the symptom evaluation unit 22 waits for the new symptom (step S5).

The symptom evaluation process 2 holds the set F of all symptoms which were input. Further, the symptom evaluation process 2 holds the cause hypothesis D(F U {f}) in the case of addition of the symptom f to the set F of the symptoms. Accordingly, when the new symptom is the symptom f in step S6 (YES), the cause hypothesis D(F U {f}) is immediately sent to the UI control processing unit 1 (step S8) and this process is completed. On the other hand, when the new symptom is different from the symptom f in step S6 (NO), the new symptom is added to the set F of the symptoms (step S7).

Further, the process is returned to the step 2 after addition of the new symptom to the set F. That is, the cause hypotheses D(F) and D(F U {f}) are sequentially obtained by the hypothesis preparation unit 21 (step S2), and the symptom evaluation E(fi:F) is obtained by the symptom evaluation unit 22 (step S3). Still further, the result of the symptom evaluation E(fi:F) is sent to the UI processing unit 1 (step S4), and the evaluation process waits for next new symptom (step S5).

The diagnostic knowledge which are held in each symptom evaluation process 2 are different dependent on the symptom fi. That is, the function Di (expressed by Di (F)=D (FU {fi})) and the function Ei (expressed by Ei (F)=E(fi:F)) are previously obtained so that it is possible to raise the execution speed. How to obtain the functions Di and Ei is different dependent on a realization method of the functions D and E. However, in general, it is possible to simplify the function and to quicken the search speed by fixing a part of an argument. For example, the function D is realized by searching the past symptom table, and the cause hypothesis is set by the occurrence frequency of each factor. In this case, since it is possible to use the table which is reduced by the symptoms only including the symptom fi, it is possible to easily realize the high speed search.

Figure 3:
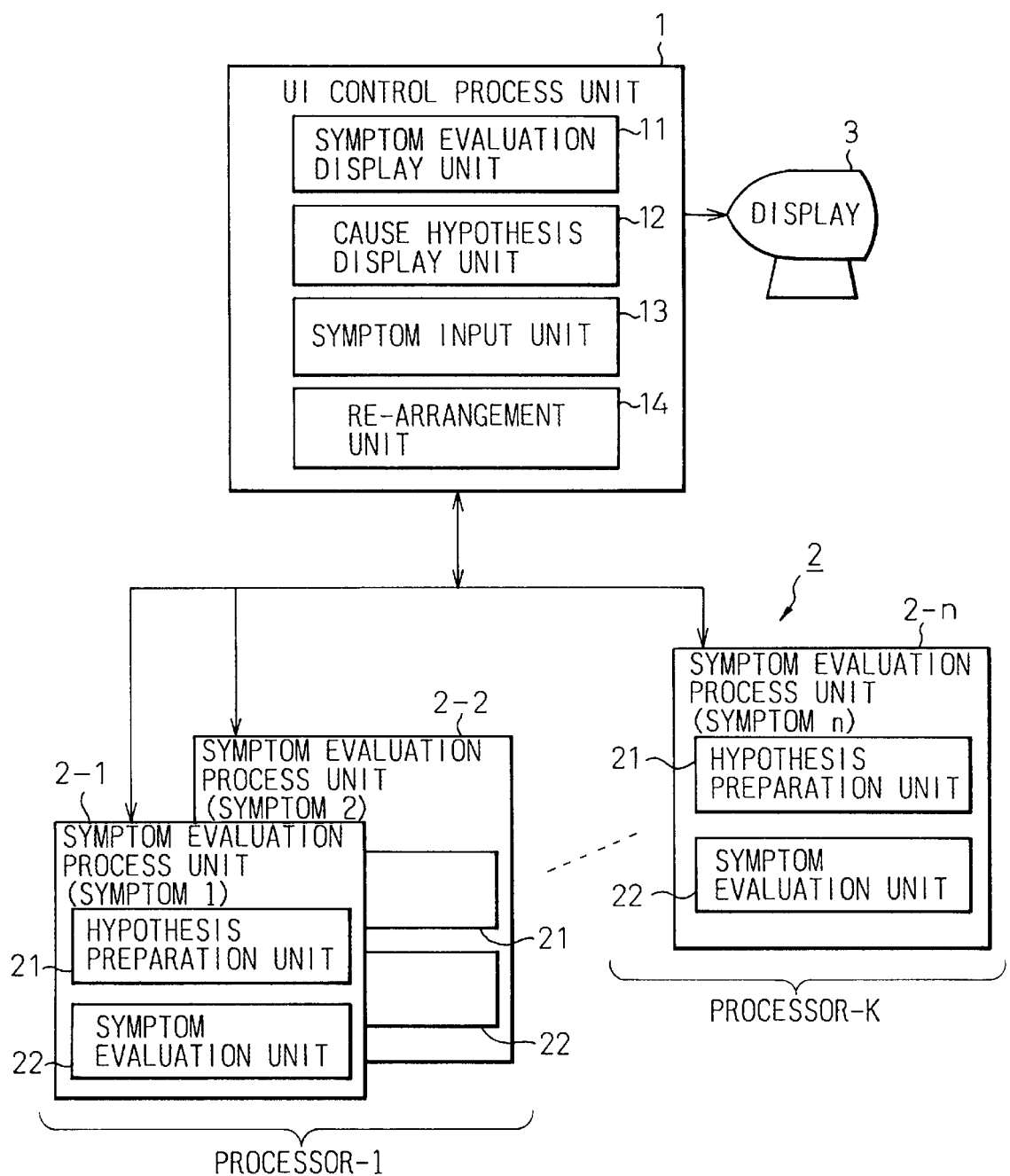
FIG. 3 is a schematic block diagram of a diagnosis apparatus according to another embodiment of the present invention.

FIG. 3 is a schematic block diagram of a diagnosis apparatus according to another embodiment of the present invention. The same reference numbers used in FIG. 1 are attached to the same components of this drawing. As is obvious, the UI control processing unit 1 further includes a re-arrangement unit 14. The re-arrangement unit is used for re-arranging the symptom evaluation processing unit 2-1 to 2-n to a predetermined number of groups, for example, k groups, corresponding to the number of processors. The operation of the re-arrangement unit 14 will be explained in detail below.

Figure 4:
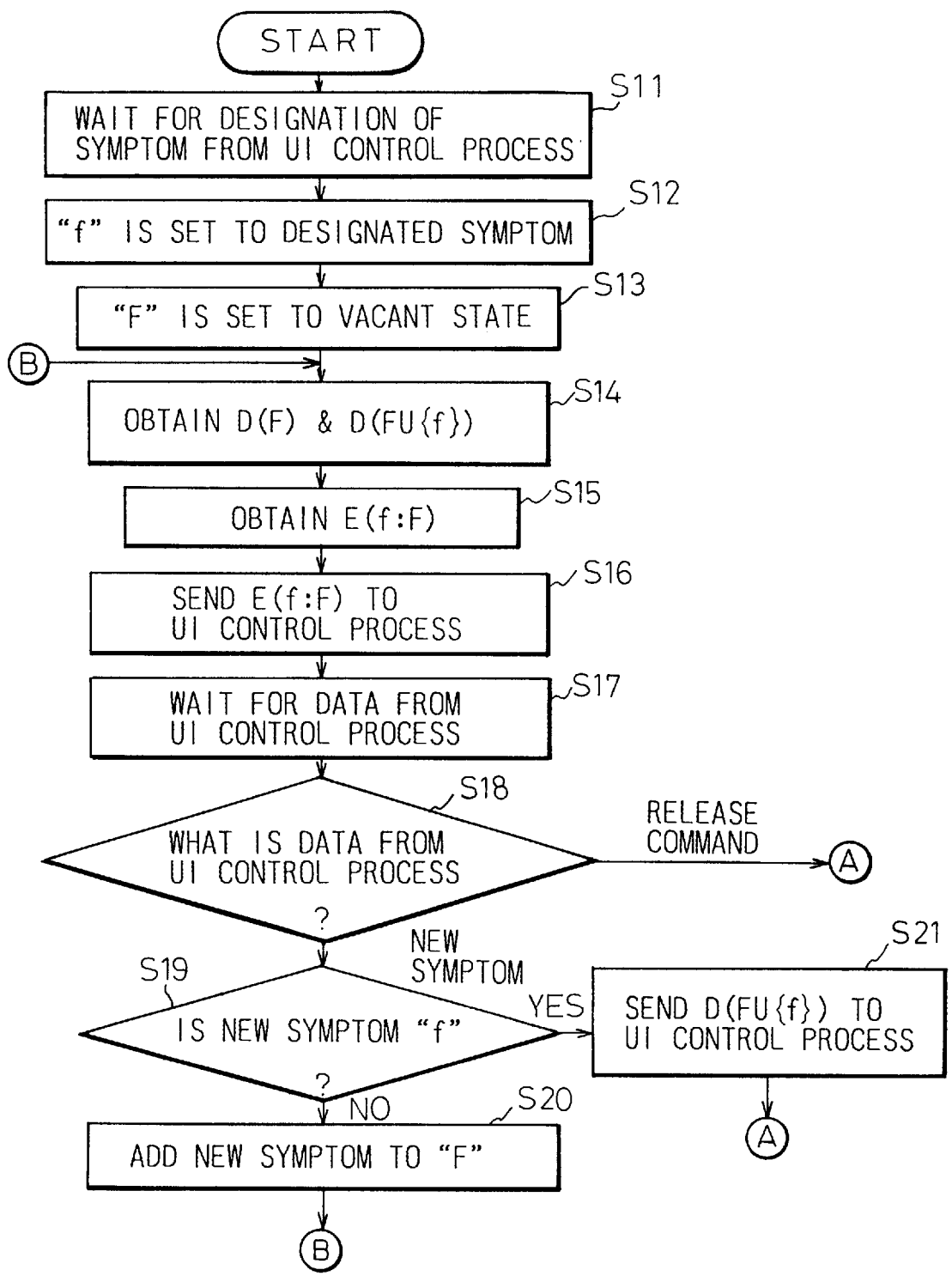
FIGS. 4 and 5 are operation flowcharts of the symptom evaluation process in FIG. 3.
Figure 5:
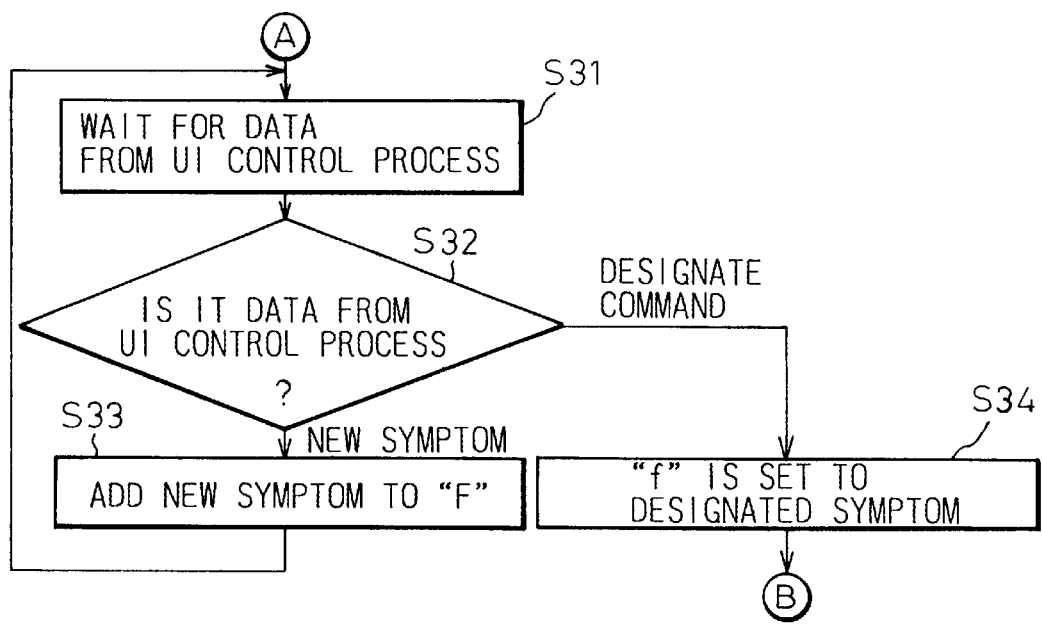

FIGS. 4 and 5 are operation flowcharts in the symptom evaluation process in FIG. 3. Although the symptom which is carried by the symptom evaluation process unit is previously determined in the case of FIG. 2, the symptom is initially determined (step S12) by receiving the designation from the UI control processing unit (step S11). When the symptom "f" is sent from the UI control processing unit 1 to the symptom evaluation processing unit 2, the symptom evaluation process waits for the designation of the symptom (step S34) and executes update of the set F of the symptoms (step S33). Since the following steps from S13 to S16 are the same as steps from S1 to S4 of FIG. 2, the explanation is omitted.

Further, the symptom evaluation processing unit 2 waits for next data from the UI control processing unit 1 (step S17). When the data is the release command (step S18), the symptom evaluation processing unit 2 releases the symptom and waits for next data therefrom (step S31). When the data from the UI control processing unit is the new symptom (step S18), whether the new symptom is "f" is determined (step S19).

When the new symptom is "f" (YES), the cause hypothesis D(F U {f}) is sent to the UI control processing unit. When the new symptom is not the symptom f (NO), the new symptom is added to the set F (step S20). After step S31, when the data from the UI control processing unit indicates the designation of the symptom (step S32), the symptom evaluation process unit sets "f" to the symptom which is designated by the UI control processing unit 1 (step S34). When the data from the UI control processing unit indicates the new symptom, the new symptom is added to the set F (step S33).

Figure 6A:
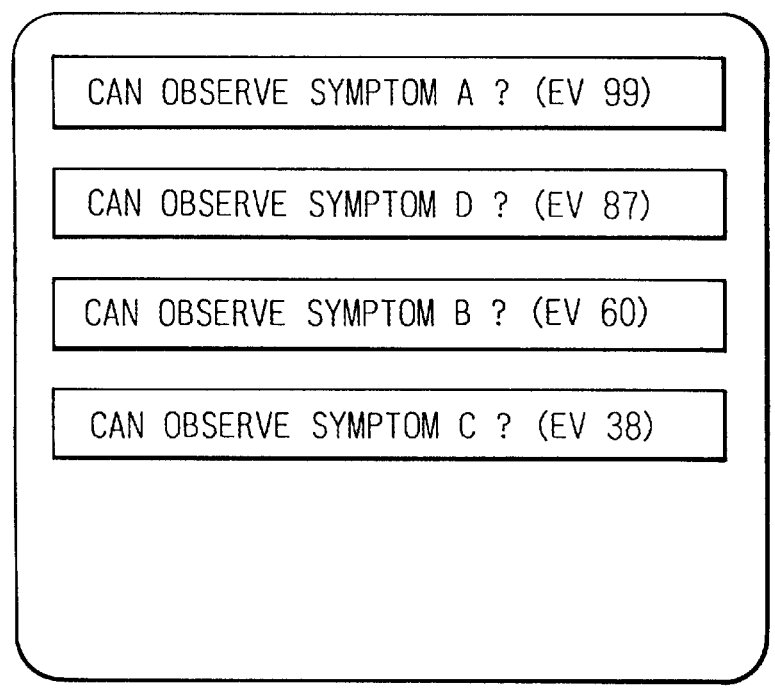
FIGS. 6A and 6B are one example of a display of the symptom evaluation.
Figure 6B:
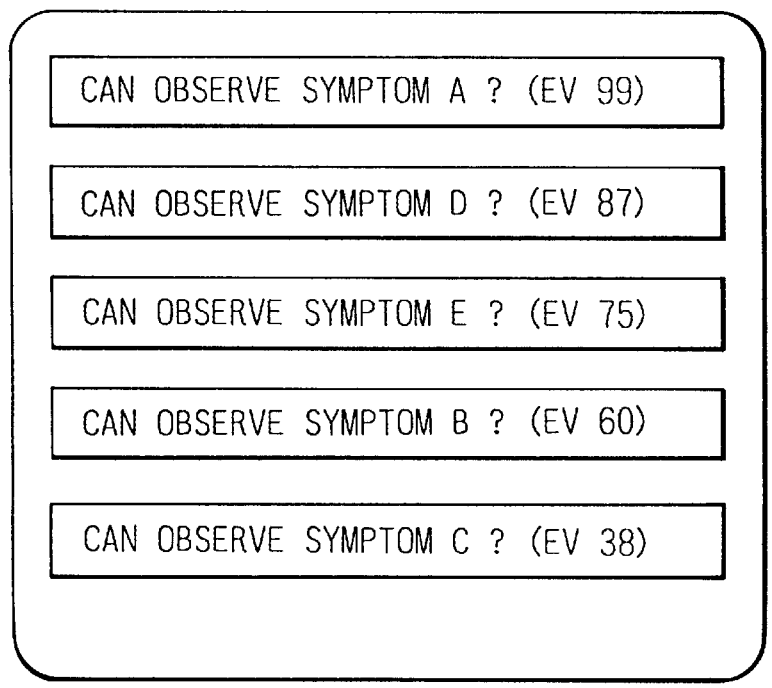
Figure 7A:
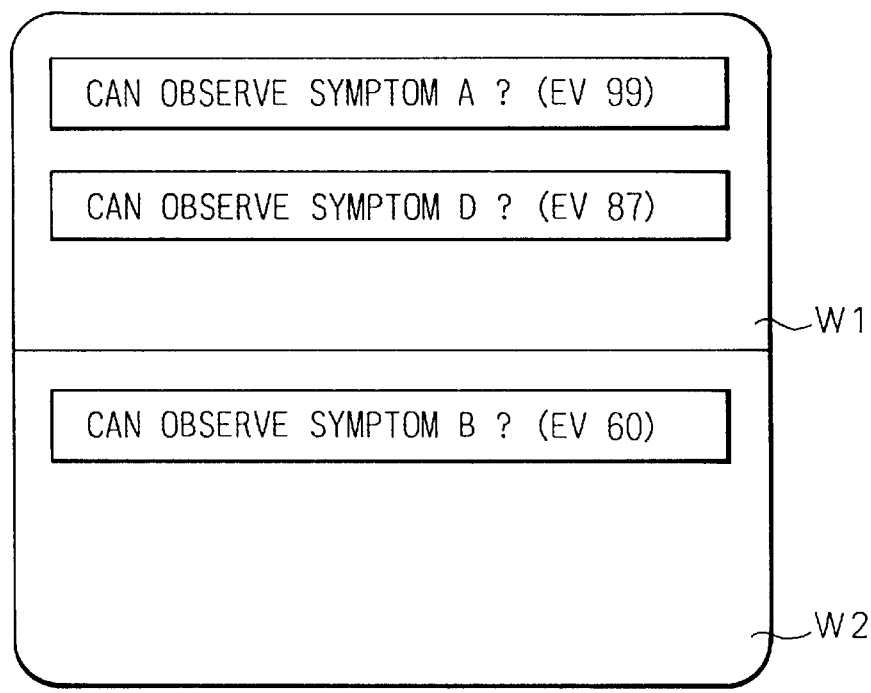
FIGS. 7A and 7B are another example of a display of the symptom evaluation.
Figure 7B:
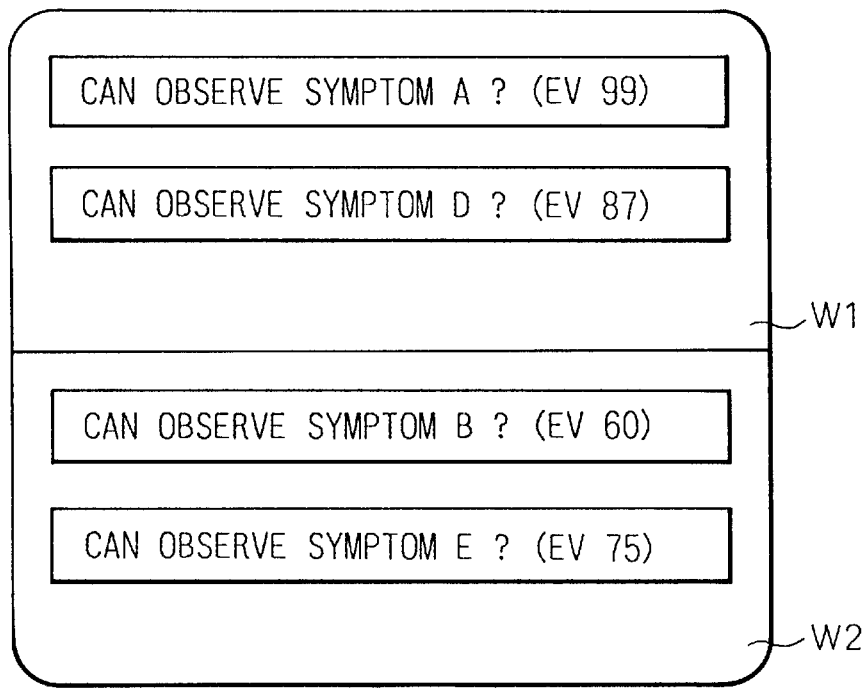

FIGS. 6A and 6B are one example of display of the symptom evaluation, and FIGS. 7A and 7B are another example of display of the symptom evaluation.

In FIG. 6A, "A" to "D" denote the symptom, and EV denotes the evaluation value for each symptom A to D. The sentence "Can observe the symptom A ?" is displayed on a screen of the display apparatus 3. Further, in this embodiment, the evaluation values EV are displayed in order of larger values 99, 87, 60 and 38. Accordingly, the user can easily watch the upper evaluation value on the screen.

In FIG. 6B, when the evaluation of the symptom "E" is completed, and the result of the evaluation is the value 75, this symptom "E" is displayed between the symptom D (EV 87) and the symptom B (EV 60) by using "scrolling operation" of the screen.

In FIG. 7A, if the display apparatus 3 does not include a function of the scrolling, the screen is divided into a pluarity of windows. In this example, two windows W1 and W2 are provided on the screen in accordance with grade of importance of evaluation (i.e., the higher evaluation value, the more important). The window W1 is applied for the most important evaluation values which exceed the value 80. The window W2 is applied to the evaluation values over the value 50 until the value 80, and the window W3 (not shown) is applied to the evaluation values under the value 50.

In FIG. 7B, the result of the evaluation is displayed on the screen. The window W1 displays the evaluation values 99 and 87 as the most important evaluation, and the window W2 displays the evaluation values 60 and 75 as the next important evaluation.

In the embodiment of FIGS. 7A and 7B, three importance groups are provided in accordance with experience of the user. However, it is possible to forcedly provide a threshold value for the grade of importance, for example, one third ($\frac{1}{3}$) position of all evaluation values as the first threshold value, and two third ($\frac{2}{3}$) position of all evaluation values as the second threshold value.

We claim:

1. A diagnosis apparatus, comprising:

display means for receiving symptoms input by a user;

user interface (UI) control processing means, operatively connected to the display means, for receiving from the display means the symptoms and for sequentially broadcasting the symptoms, said UI control processing means comprising a symptom evaluation display unit, and a cause hypothesis display unit; and a plurality of symptom evaluation processing means, each of the plurality of symptom evaluation processing means being separately provided for a corresponding one of the symptoms and being operatively connected in parallel with each other, and each of the plurality of symptom evaluation processing means for receiving the corresponding one of the symptoms broadcast by the UI control processing means, for calculating a hypothesis of possible causes for the corresponding one of the symptoms, and for evaluating, based on the hypothesis, the corresponding one of the symptoms to determine a contribution rate of one of the symptoms to execute an optimum search operation of the symptoms, each of the plurality of symptom evaluation processing means corresponding to one of the symptoms and the user imputing additional symptom, and evaluating how the corresponding hypothesis is improved when each corresponding one of the symptoms is input by the user.

2. A diagnosis apparatus as claimed in claim 1, wherein said UI control processing means comprises:

a symptom evaluation display unit for receiving results of evaluation from the symptom evaluation processing means, and outputting them to the display means in order to support selection of the symptom by the user;

a cause hypothesis display unit for receiving the cause hypothesis sent from the particular symptom evaluation process, and outputting it to the display means in order to inform the cause hypothesis to the user; and a symptom input unit for broadcasting the symptom selected by the user to all symptom evaluation processing.

3. A diagnosis apparatus as claimed in claim 1, wherein each of said symptom evaluation process means comprises:

a hypothesis preparation unit for obtaining the cause hypotheses $D(F)$ and $D(F \cup \{f\})$ for a set "F" of symptoms and a symptom "f"; and a symptom evaluation unit for obtaining an evaluation $E(f:F)$ of the symptom "f" for the set F of the symptoms by using the cause hypotheses.

4. A diagnosis apparatus as claimed in claim 2, wherein said UI control processing means further comprises a re-arrangement unit for re-arranging the symptom evaluation processing means into a predetermined number of groups corresponding to a number of processors executing the symptom evaluation processing means.

5. A diagnosis apparatus as claimed in claim 2, wherein said symptom evaluation display unit displays evaluation values sent from the symptom evaluation processing means in the order of importance on a screen of the display apparatus.

6. A diagnosis apparatus as claimed in claim 5, wherein the symptom evaluation display unit divides the evaluation values into a predetermined number of groups in the order of importance, and displays them on the screen.

7. A diagnosis apparatus as claimed in claim 3, wherein when the symptom carried out by the symptom evaluation unit is previously and fixedly determined for each unit, the symptom evaluation unit holds a determined symptom as the symptom to be carried out.

8. A diagnosis apparatus as claimed in claim 3, wherein load distribution of the system is performed by dynamic re-arrangement of the symptom carried out by the symptom evaluation unit.

* * * * *